United States Patent

Tsukamoto et al.

Patent Number: 5,403,931
Date of Patent: Apr. 4, 1995

[54] (−)-(S)-2,8-DIMETHYL-3-METHYLENE-1-OXA-8-AZASPIRO[4.5]DECANE L-TARTRATE

[75] Inventors: Shin-ichi Tsukamoto, Ibaraki; Takeru Kohinata, Saitama; Mitsuo Fujii, Ibaraki; Sakiko Tomizawa, Gunma; all of Japan

[73] Assignee: Yamanouchi Pharmaceutical Co., Ltd., Tokyo, Japan

[21] Appl. No.: 146,133
[22] PCT Filed: Apr. 27, 1992
[86] PCT No.: PCT/JP92/00548
    § 371 Date: Nov. 12, 1993
    § 102(e) Date: Nov. 12, 1993
[87] PCT Pub. No.: WO92/20683
    PCT Pub. Date: Nov. 26, 1992

[30] Foreign Application Priority Data

May 15, 1991 [JP] Japan .................. 3-139619

[51] Int. Cl.⁶ ............... C07D 491/107; A61K 31/445
[52] U.S. Cl. ............................. 546/16; 514/278
[58] Field of Search ..................... 546/16; 514/278

[56] References Cited

U.S. PATENT DOCUMENTS 4,996,210  2/1991  Tsukamoto .................. 514/278
5,075,317  12/1991 Wu ............................ 514/278

Primary Examiner—Celia Chang
Attorney, Agent, or Firm—Sughrue, Mion, Zinn, Macpeak & Seas

[57] ABSTRACT (−)-(S)-2,8-Dimethyl-3-methylene-1-oxa-8-azaspiro[4.5]decane L-tartrate having the following structural formula:

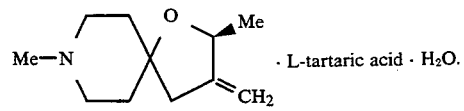

The compound exhibits a selective affinity for the muscarinic acetylcholine receptor and has a storage stability superior to that of other salts.

1 Claim, 4 Drawing Sheets

(−)-(S)-2,8-DIMETHYL-3-METHYLENE-1-OXA-8-AZASPIRO[4.5]DECANE L-TARTRATE

TECHNICAL FIELD

The present invention relates to (−)-(S)-2,8-dimethyl-3-methylene-1-oxa-8-azaspiro[4.5]decane (hereinafter referred to briefly as compound A) L-tartrate monohydrate which is of value as a medicament and to a process for producing the same compound.

BACKGROUND ART

It has been reported that compound A has a selective affinity for the muscarinic acetylcholine receptor (M1 receptor) and hydrochloride, fumarate, maleate and di-p-toluoyl-D-tartrate of compound A can be utilized in the treatment of diseases associated with a deficiency of acethylcholine-related functions, such as Alzheimer's disease (JP-A-2-36183; the term "JP-A" as used herein means an "unexamined published Japanese patent application").

JP-A-2-36183 enumerates various inorganic and organic acid addition salts which can be formed by heterocyclic spiro compounds such as compound A, including addition salts with tartaric acid. However, the literature contains no specific disclosure of the tartrate of compound A or its monohydrate.

On the other hand, compound A as the free base is oily and can be crystallized after conversion to certain acid addition salts. The research undertaken by the inventors of the present invention revealed that compound A does not form a crystallizable salt with D-tartaric acid, D- or L-malic acid, succinic acid, hydrobromic acid, sulfuric acid, phosphoric acid or the like. The hydrochloride gave a powdery compound which, however, underwent deliquescence within 24 hours when allowed to stand in the air, due to high hygroscopicity.

Meanwhile, stability of compound A is low even in the form of a solid salt and this instability has been a major drawback in the practical application of this compound as a medicinal material.

DISCLOSURE OF INVENTION

After extensive studies under these circumstances, the inventors of the present invention found surprisingly that the L-tartrate monohydrate of compound A is crystallizable and also highly stable. The present invention was accomplished based on this finding.

The present invention is, therefore, directed to compound A L-tartrate monohydrate. The invention is further directed to a process for producing compound A L-tartrate monohydrate comprising dissolving 2,8-dimethyl-3-methylene-1-oxa-8-azaspiro[4.5]decane and L-tartaric acid in an aqueous organic solvent and carrying out crystallization.

The aqueous organic solvent which can be used in the process of the present invention is any solvent that is capable of dissolving the starting compounds. Representative examples of the aqueous organic solvent includes aqueous alcohols such as aqueous methanol, aqueous ethanol, aqueous propanol, aqueous isopropyl alcohol, etc., aqueous acetonitrile, and mixtures thereof. Regarding the water content of said aqueous solvent, 9 parts by volume of the organic solvent or solvents to 1 part by volume of water is preferred, but the water content is not limited to this ratio.

For an enhanced solubility of the starting compounds, the system is preferably heated at a suitable temperature.

The starting compound, 2,8-dimethyl-3-methylene-1-oxa-8-azaspiro[4.5]decane, may be whichever of its optically active compounds and racemic compound. When the racemic compound is employed, the resulting L-tartrate can be recrystallized in repetition to isolate the desired pure compound A L-tartrate monohydrate.

The compound A L-tartrate monohydrate thus produced is remarkably superior to other salts of compound A in stability. Its shelf-life at room temperature is not less than 3 years, which is sufficient to insure the application of compound A as a treating agent.

INDUSTRIAL APPLICABILITY

The stability of the compound of the present invention is now described in further detail in comparison with the sesquifumarate which is the most stable salt of compound A heretofore available.

Test method

Under protection from light, the respective compounds were stored for 3 months in the open condition at 40° C., 50° C. and 60° C. or in the condition of 75% RH at 40° C.. The changes in appearance and in the residual amount determined by chromatography were investigated. The results are shown in Table 1.

Also shown are the expected stability values of these compounds at room temperature (25° C.) as calculated by the Lordi method [N. G. Lordi et al., J. Pharm. Sci., 54, 531 (1956)] described hereinafter.

TABLE 1

| | | Changes in residual amount (%) and in appearance | | | | |
| | | Storage Conditions | | | | |
| Test Compound | Storage Period | 40° C. Open | 50° C. Open | 60° C. Open | 40° C., 75% RH | $t^{25}_{90}$ Value (Note 1) |
| --- | --- | --- | --- | --- | --- | --- |
| Compound A L-Tartrate Monohydrate | 1 Month | 99.8 (%) (−) | 99.9 (%) (−) | 98.7 (%) (−) | 100.2 (%) (−) | ≧40 Months |
| | 2 Months | 100.9 (%) (−) | 100.2 (%) (−) | 97.7 (%) (+1) | 99.8 (%) (−) | ≧40 Months |
| | 3 Months | 99.4(%) (−) | 98.8 (%) (−) | 94.3 (%) (+2) | 97.5 (%) (+1) | ≧40 Months |
| Compound A Sesquifumarate | 1 Month | 97.5 (%) (+1) | 92.5 (%) (+2) | 90.5 (%) (+2) | 95.4 (%) (+2) | 16 Months |
| | 2 Months | 95.2 (%) (+2) | 91.2 (%) (+2) | 88.6 (%) (+3) | 83.3 (%) (+3) | 11 Months |
| | 3 Months | 94.0 (%) (+2) | 90.7 (%) (+2) | 85.3 (%) (+3) | 43.1 (%) (+4) | 13 Months |

In the table, the symbol in parentheses denotes the degree of change in appearance according to the following criteria.

(−): no change (white crystal)
(+): white with a slight pale yellowish tinge
(+2): pale yellowish white
(+3): yellow brown
(+4): brown (Note 1) The time period (in months) for which a residue value of 90% can be assured at 25° C. was calculated by means of the following equation according to Lordi et al.

$$\log tT_1 = 2 \log tT_2 - \log tT_0$$

Using the data at 40° and 60° C. as $T_1$ and $T_2$, respectively, the stability value at 25° C. ($T_0=25$) was calculated.

It is apparent from the above results that the compound of the invention is superior to the sesquifumarate in stability and is particularly stable in a high-humidity environment. Moreover, the period of time (in months) till the residue value becomes 90% residue when stored at 25° C. as calculated by the Lordi method was not less than 40 months.

BEST MODE OF CARRYING OUT THE INVENTION

The following examples are intended to further describe the compound and process of the present invention. The process for producing compound A sesquifumarate is also given as a reference example.

Reference Example

To 70 ml of ethanol were added 24.39 g of (−)-(S)-2,8-dimethyl-3-methylene-1-oxa-8-azaspiro[4.5]decane and 27.3 g of fumaric acid and the mixture was heated to prepare a homogeneous solution. The solution was allowed to cool and maintained at 4° C. for about 15 hours. The resulting crystals were collected by filtration and dried under reduced pressure to give 47 g of (−)-(S)-2,8-dimethyl-3-methylene-1-oxa-8-azaspiro[4.5]decane sesquifumarate.

This compound has the following physicochemical properties.

1) Elemental analysis (for $C_{17}H_{25}NO_7$) c (%) H (%) N (%) Calcd.: 57.45 7.09 3.94 Found: 57.43 7.15 3.88

2) Melting point: 128.5°–129.5° C.

3) Optical rotation $[\alpha]_D^{20}$ −29.2° (C=1.11, methanol)

Figure 3:
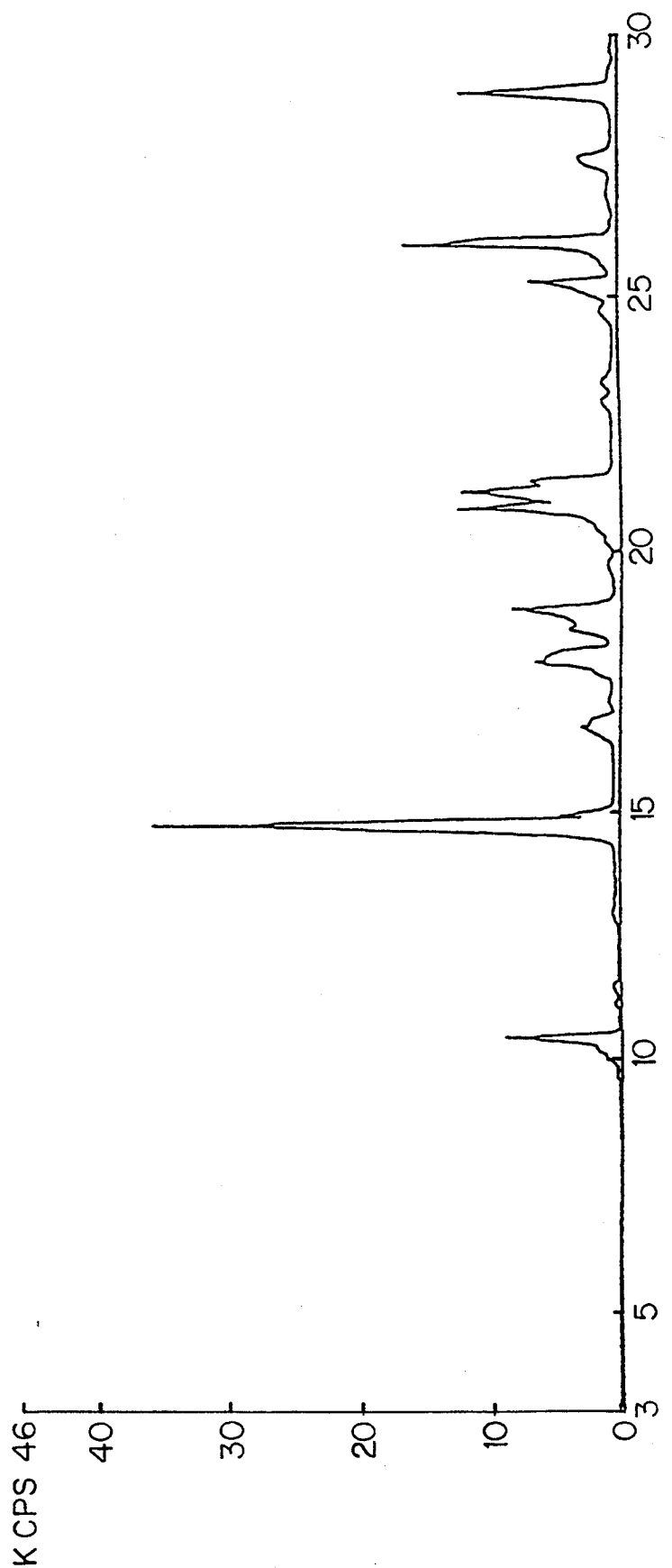
FIG. 3 shows a powder X-ray diffraction pattern of compound A sesquifumarate.

4) Powder X-ray diffraction analysis (target: Cu; tube voltage: 40 KV; tube current: 40 mA) FIG. 3

Figure 4:
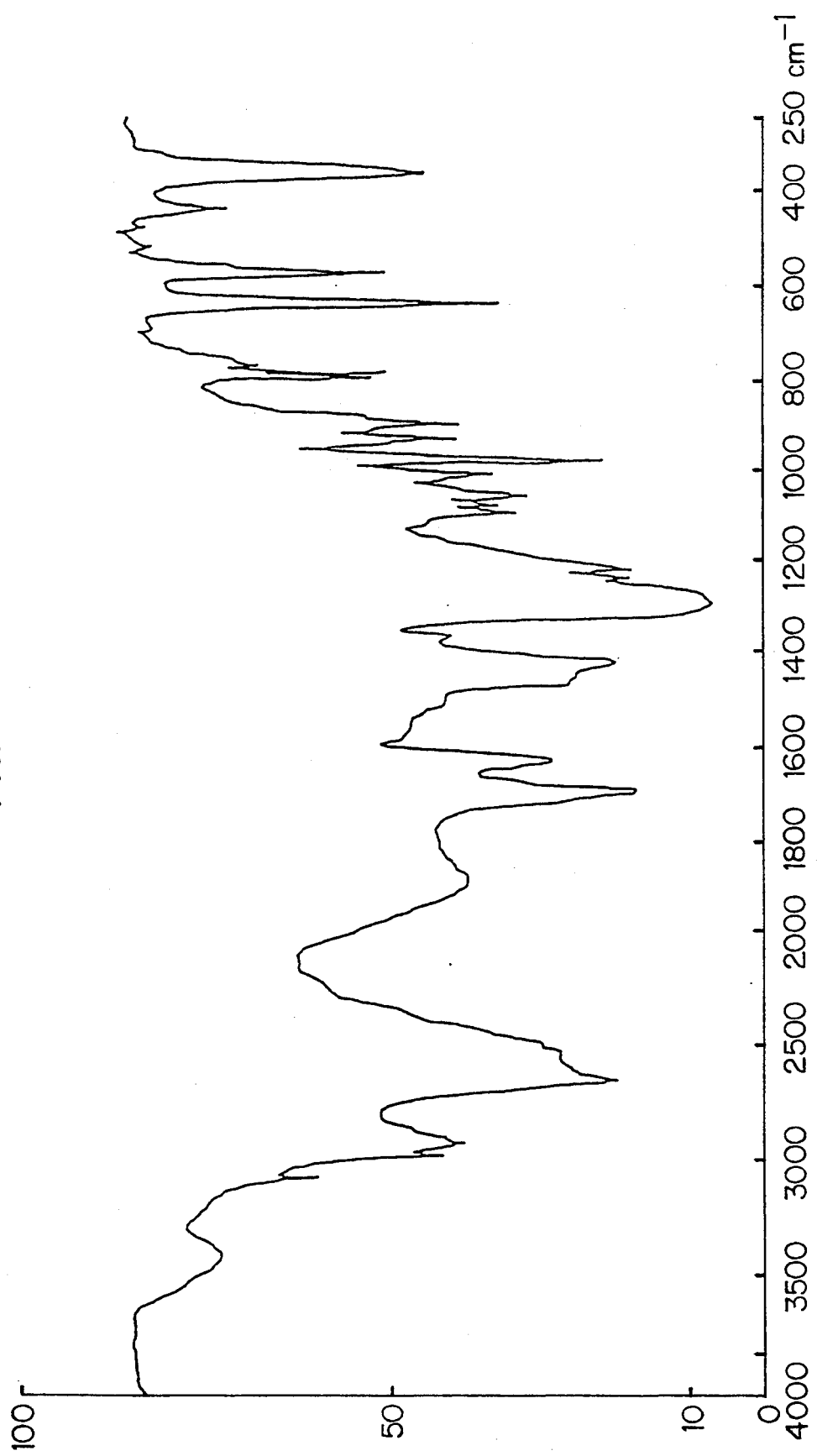
FIG. 4 shows an infrared absorption spectrum (the KBr method) of compound A sesquifumarate.

5) Infrared absorption spectrum (the KBr method) FIG. 4

EXAMPLE 1

To 90% aqueous ethanol (water:ethanol = 1:9, v/v), 7 g of (±)-2,8-dimethyl-3-methylene-1-oxa-8-azaspiro[4.5]decane and 5.79 g of L-tartaric acid were added and dissolved by heating at 60° C. The resulting solution was allowed to cool and maintained at about 4° C. for 15 hours. The resulting crystals were collected by filtration and, without drying, recrystallized from 9 ml of 90% aqueous ethanol. This recrystallization procedure was repeated further twice and the crystals obtained were dried under reduced pressure to give 3.22 g of (−)-(S)-2,8-dimethyl-3-methylene-1-oxa-8-azaspiro[4.5]decane L-tartrate monohydrate.

This compound has the following physicochemical properties.

1) Elemental analysis (for $C_{15}H_{25}NO_7 \cdot H_2O$) C (%) H (%) N (%) Calcd.: 51.57 7.79 4.01 Found: 51.44 7.75 3.91

2) Melting point 97° C.

3) Optical rotation $[\alpha]_D^{20}$ −16.4° (C=0. 988, methanol)

Figure 1:
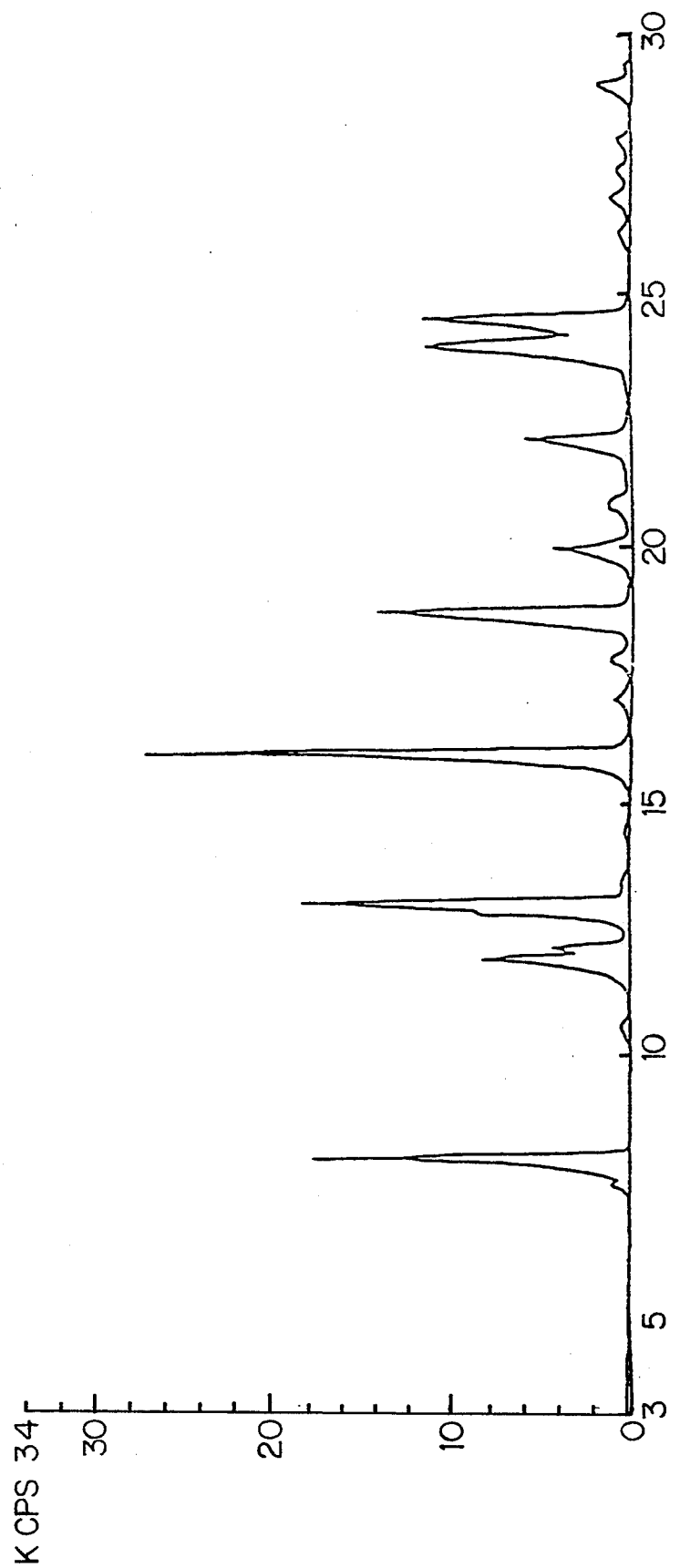
FIG. 1 shows a powder X-ray diffraction pattern of compound A L-tartrate monohydrate.

4) Powder X-ray diffraction analysis (target: Cu; tube voltage: 40 KV; tube current: 40 mA) FIG. 1

Figure 2:
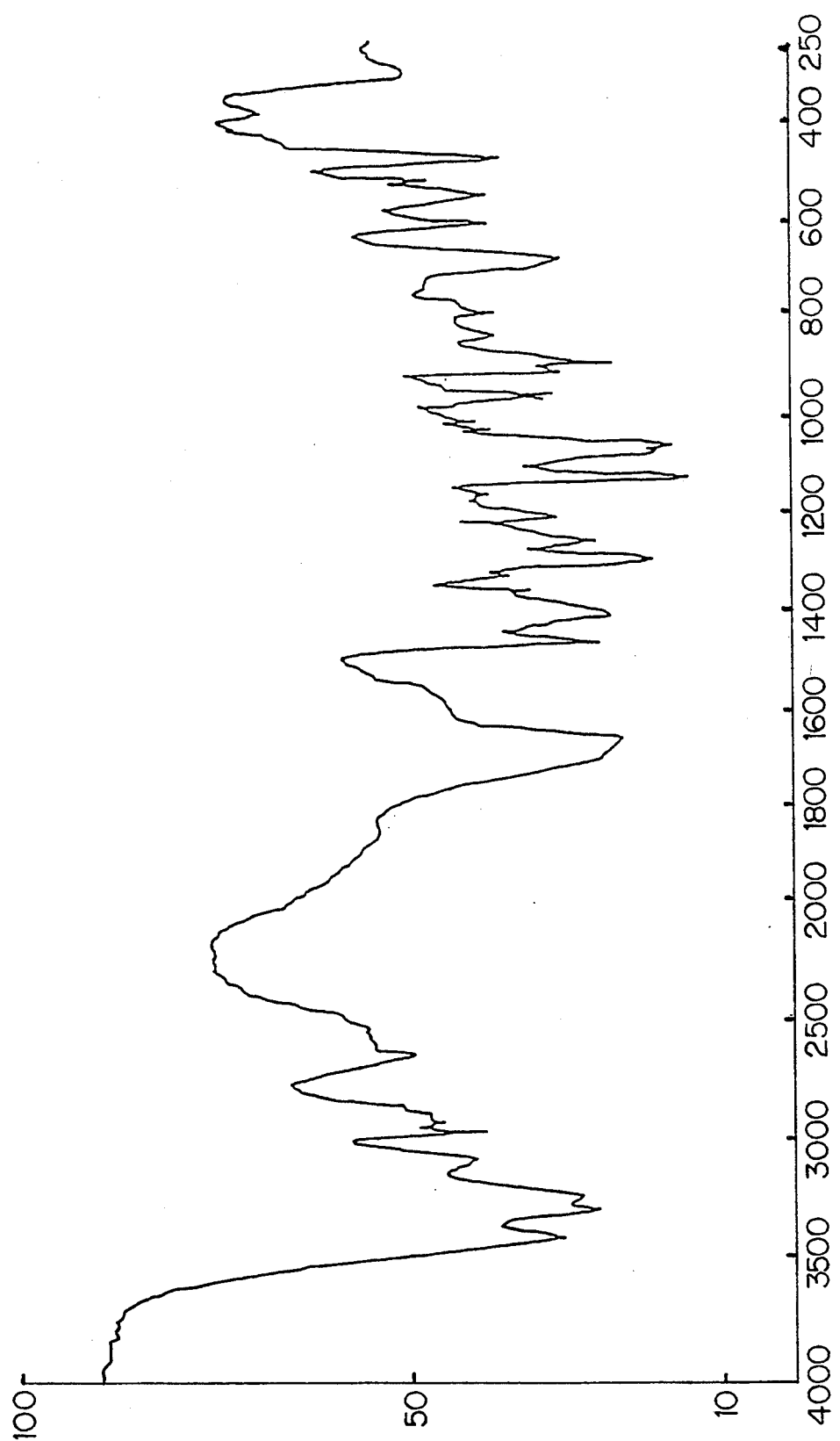
FIG. 2 shows an infrared absorption spectrum (the KBr method) of compound A L-tartrate monohydrate.

5) Infrared absorption spectrum (the KBr method) FIG. 2

EXAMPLE 2

To 28 l of 90% aqueous ethanol (water:ethanol = 1:9, v/v), 7.74 kg of L-tartaric acid was added and dissolved by heating at 65° C. To the resulting solution was added 9.41 kg of (−)-(S)-2,8-dimethyl-3-methylene-1-oxa-8azaspiro[4.5]decane dropwise. The mixture was allowed to cool and maintained for crystallization at 0° C. for 15 hours. The resulting crystals were collected by filtration and dried under reduced pressure to give 14.76 kg of (−)-(S)-2,8-dimethyl-3-methylene-1-oxa-8-azaspiro[4.5]decane L-tartrate monohydrate. The physicochemical properties of this compound were in agreement with those of the compound obtained in Example 1.

We claim:

1. (−)-(S)-2,8-Dimethyl-3-methylene-1-oxa-8-azaspiro[4.5]decane L-tartrate monohydrate.

* * * * *